US008463388B2

(12) United States Patent
Wei

(10) Patent No.: US 8,463,388 B2
(45) Date of Patent: Jun. 11, 2013

(54) ELECTRONIC LOW-FREQUENCY PULSE PATCH OF A ONE-PIECE STRUCTURE AND METHOD FOR MANUFACTURING THE SAME

(75) Inventor: Tuan Wei, Taipei (TW)

(73) Assignee: Hivox Biotek Inc. (TW)

( * ) Notice: Subject to any disclaimer, the term of this patent is extended or adjusted under 35 U.S.C. 154(b) by 741 days.

(21) Appl. No.: 12/719,976

(22) Filed: Mar. 9, 2010

(65) Prior Publication Data

US 2011/0224754 A1 Sep. 15, 2011

(51) Int. Cl.
*A61N 1/36* (2006.01)
*A61N 1/04* (2006.01)

(52) U.S. Cl.
CPC .......... *A61N 1/0404* (2013.01); *A61N 1/36021* (2013.01)
USPC ............................................................ 607/46

(58) Field of Classification Search
USPC .............. 600/372, 382, 393; 607/46, 72, 115, 607/148, 149
See application file for complete search history.

(56) References Cited

U.S. PATENT DOCUMENTS 5,578,065 A * 11/1996 Hattori et al. .................. 607/46
5,991,655 A * 11/1999 Gross et al. ..................... 604/20
D575,748 S * 8/2008 Youm .......................... D13/171
2008/0065182 A1* 3/2008 Strother et al. ............... 607/115

FOREIGN PATENT DOCUMENTS

GB 2478787 A * 9/2011

* cited by examiner

*Primary Examiner* — Carl H Layno
*Assistant Examiner* — Jessica Sarcione

(57) ABSTRACT

An electronic low-frequency pulse patch of a one-piece structure comprises a flexible top cover body, a hollow supporting enclosure, a circuit control unit, a power supply unit, a base and a coupling output conductive flexible film. Flexible top cover body is coupled to the coupling output conductive flexible film with hollow supporting enclosure located therebetween. Circuit control unit and the power supply unit are coupled to the base for providing respective low-frequency electric pulses. Electrical conduction is accomplished by electrically connecting the first and the second conductive ends of the base to respective conductive contact lugs of the coupling output conductive flexible film. At either side of which, first and second low-frequency pulse output regions are disposed, such that the electronic low-frequency pulse patch is bendable for conforming to curvature at different locations of the human body without using screw or other means.

19 Claims, 6 Drawing Sheets

30
31
313
311
312
322
32
373
37
33
34
35
36
321
371
372

ELECTRONIC LOW-FREQUENCY PULSE PATCH OF A ONE-PIECE STRUCTURE AND METHOD FOR MANUFACTURING THE SAME

BACKGROUND OF THE INVENTION

1. Technical Field

The present invention relates to a patch for pain treatment and relieving, and more particularly, to an electronic low-frequency pulse patch of a one-piece structure having a simple structure in which electronic circuitry and mechanical appearance are formed integrally, being adapted to be attached to a human body and being bendable. This electronic low-frequency pulse patch of a one-piece structure can be applied to various electronic patches for treating or relieving pain.

2. Description of Related Art

A feeling of aching pain often arises after one has worked for an extended period of time or has taken strenuous exercises. According to a lot of information that had been verified or disclosed by documents published at home and abroad as well as by the Food and Drug Administration (FDA) of America, low-frequency pulses are effective in treating or relieving the pain, although this will not be further described herein. For this reason, most of low-frequency massage pads available in the market comprise a piece of conductive fabric intended to make contact with a human body and a function selection controller electrically connected to the conductive fabric via a conductive wire. However, use of the conductive wire causes inconveniences in use; even further, use of the conductive wire imposes a limitation on the distance from a user to a host machine, making it inconvenient to use when the patient is positioned at a certain distance from the host machine.

Furthermore, such a low-frequency massage pad with a function selection controller and a piece of conductive cloth is relatively costly to manufacture because it is provided with a plurality of frequency control functions; and the function selection controller has a certain volume, which makes it inconvenient for the user to carry the massage pad for use. As a consequence, it is difficult to put such a low-frequency massage pad into practical use.

Accordingly, a kind of wireless portable low-frequency treatment unit has been developed. For example, an electronic acupuncture and moxibustion device of a quick-attachment structure is disclosed in Taiwan Patent No. 246840, according to which a hard plastic enclosure is used to assemble batteries and an output circuit (portion) therein and is then joined to a conductive patch by means of a metallic fastener. However, the human body has different curvature at different sites, so the hard enclosure must be made separately from the patch and then, by means of the metallic fastener, fixed to the conductive patch before the device as a whole is attached to a specific site on the human body. This is very inconvenient, adds to the implementation complexity and discourages the user from using such a device, making it difficult to put such a device into practical use. Furthermore, as it requires use of a lot of elements, the manufacturing cost is increased. Moreover, difficulty in bending the metallic fastener makes it inconvenient to operate by the user.

To solve the afore-mentioned problems, a conventional electronic low-frequency pulse patch of a one-piece structure has been proposed. Referring to FIG. 1, there is shown an exploded structural view of the conventional electronic low-frequency pulse patch of a one-piece structure. As shown, the conventional electronic low-frequency pulse patch of a one-piece structure 10 comprises a flexible top cover body 11 as an enclosure, in which a first receiving space 12 and a second receiving space 13 are formed. The first receiving space 12 has a power supply unit 14 disposed therein to supply power necessary for operation of the electronic low-frequency pulse patch of a one-piece structure 10 that is flexible and water proof. Above the power supply unit 14 inside the first receiving space 12 is disposed a first push switch 15 configured to control operation of the power supply unit 14. Below the power supply unit 14 is disposed a first pole low-frequency output unit region 17. The second receiving space 13 is disposed with a support structure 16 in the internal thereof, and a second push switch 151 is disposed on the support structure 16 for controlling the operation of the support structure 16. Moreover, a second pole low-frequency output unit region 18 is disposed under the support structure 16. Between the first pole low-frequency output unit region 17 and the second pole low-frequency output unit region 18 is disposed a flexible ribbon cable assembly 19 adapted to establish electrical connection between the first pole low-frequency output unit region 17 and the second pole low-frequency output unit region 18. Below the flexible top cover body 11 is covered a coupling output conductive flexible film 20 made of polyester (PET). In the coupling output conductive flexible film 20 are formed a first opening 201 and a second opening 202 disposed corresponding to the first pole low-frequency output unit region 17 and the second pole low-frequency output unit region 18 respectively so that specific portions of the first pole low-frequency output unit region 17 and the second pole low-frequency output unit region 18 are exposed through the first opening 201 and the second opening 202. Hence, the specific portions of the first pole low-frequency output unit region 17 and the second pole low-frequency output unit region 18 can be electrically coupled with a first pole coupling conductive patch 21 and a second pole coupling conductive patch 22 and also can be attached to the user's skin to perform low-frequency massage thereon.

During use of such an electronic low-frequency pulse patch of a one-piece structure 10 on a human body, damage, poor contact and even open-circuit tend to occur to the flexible ribbon cable assembly 19 of the patch 10 due to frequent bending to conform to the human body's curvature or due to pulling or bending by an external force, causing failure of the electronic low-frequency pulse patch of a one-piece structure 10. Therefore, it is difficult to put such a patch into practical use. Moreover, design of such a patch does not allow for replacement of the batteries, and once power of the batteries runs out, the patch will no longer be of use, which is very inconvenient for the user.

As described above, efforts have to been made to provide a wireless portable low-frequency treatment device that can eliminate need of using any metallic fastener to join the host unit and the conductive patch into an integrally formed flexible water-proof structure and can present prolonged service life.

BRIEF SUMMARY OF THE INVENTION

To solve the afore-mentioned problems, an electronic low-frequency pulse patch of a one-piece structure is proposed in the present invention, which has a power supply and a circuit capable of outputting positive and negative current pulses concealed therein without need of any other fastening means, and can be attached to different sites of a human body independently as desired. Additionally, as the circuit is concealed within the flexible one-piece structure and is bendable, the patch can be attached onto a human body in conformity with the human body's curvature, which makes it very easy to use and remarkably increases the popularity to users.

An electronic low-frequency pulse patch of a one-piece structure disclosed in the present invention comprises: a flexible top cover body, having a receiving space formed therein; a hollow supporting enclosure, being disposed in the receiving space, wherein above the hollow supporting enclosure are disposed a first cantilever elastic pushing end and a second cantilever elastic pushing end, both of which are coupled with an inner surface of the flexible top cover body; a control circuit unit, being disposed within the hollow supporting enclosure, wherein the control circuit unit is provided with at least one first low-frequency pulse output end, at least one second low-frequency pulse output end as well as a first control end and a second control end, and the first control end and the second control end are coupled to the first cantilever elastic pushing end and the second cantilever elastic pushing end respectively, and the pulses outputted from the at least one first low-frequency pulse output end and the at least one second low-frequency pulse output end can be adjusted according to the number of times that the first cantilever elastic pushing end and the second cantilever elastic pushing end being triggered, a power supply unit, being electrically coupled to the control circuit unit to supply power necessary for operation of the control circuit unit; a base, being joined to the bottom of the hollow supporting enclosure to fix the control circuit unit and the power supply unit into the hollow supporting enclosure, wherein the base is provided with at least one first conductive end electrically coupled to the at least one first low-frequency pulse output end and at least one second conductive end electrically coupled to the at least one second low-frequency pulse output end; and a coupling output conductive flexible film, being joined integrally to the bottom of the flexible top cover body, wherein the coupling output conductive flexible film is formed with an opening at a center thereof, at the periphery of the opening are disposed at least one first conductive contact lug electrically connected to the at least one first conductive end and at least one second conductive contact lug electrically connected to the at least one second conductive end, and on a bottom surface of the coupling output conductive flexible film are disposed a first low-frequency pulse output region electrically connected to the at least one first conductive contact lug and a second low-frequency pulse output region electrically connected to the at least one second conductive contact lug.

According to an embodiment of the present invention, a method for manufacturing an electronic low-frequency pulse patch of a one-piece structure is provided, which comprises the following steps:

providing a flexible top cover body, which has a receiving space formed therein; disposing above a hollow supporting enclosure a first cantilever elastic pushing end and a second cantilever elastic pushing end, and disposing the hollow supporting enclosure into the receiving space in such a way that both the first cantilever elastic pushing end and the second cantilever elastic pushing end are coupled with an inner surface of the flexible top cover body; disposing in a control circuit unit at least one first low-frequency pulse output end, at least one second low-frequency pulse output end as well as a first control end and a second control end in such a way that the first control end and the second control end are coupled to the first cantilever elastic pushing end and the second cantilever elastic pushing end respectively and pulses outputted from the at least one first low-frequency pulse output end and the at least one second low-frequency pulse output end can be adjusted according to the number of times that the first cantilever elastic pushing end and the second cantilever elastic pushing end are triggered; disposing the control circuit unit into the hollow supporting enclosure; providing a power supply unit, which is electrically coupled to the control circuit unit to supply power necessary for operation of the control circuit unit; disposing on a base at least one first conductive end electrically coupled to the at least one first low-frequency pulse output end and at least one second conductive end electrically coupled to the at least one second low-frequency pulse output end; forming an opening at a center of a coupling output conductive flexible film, disposing at the periphery of the opening at least one first conductive contact lug and at least one second conductive contact lug, and disposing on a bottom surface of the coupling output conductive flexible film a first low-frequency pulse output region electrically connected to the at least one first conductive contact lug and a second low-frequency pulse output region electrically connected to the at least one second conductive contact lug; and joining the base to the bottom of the hollow supporting enclosure to fix the control circuit unit and the power supply unit into the hollow supporting enclosure, and electrically connecting the first conductive contact lug to the first conductive end and electrically connecting the second conductive contact lug to the second conductive end.

BRIEF DESCRIPTION OF THE SEVERAL VIEWS OF THE DRAWINGS

The invention as well as a preferred mode of use and advantages thereof will be best understood by referring to the following detailed description of an illustrative embodiment in conjunction with the accompanying drawings, wherein:

FIG. 4(*b*) is a schematic back outline view of the control circuit unit of the present invention;

DETAILED DESCRIPTION OF THE INVENTION

Detailed disclosures and technical essence of the present invention will be described as follows.

Figure 1:
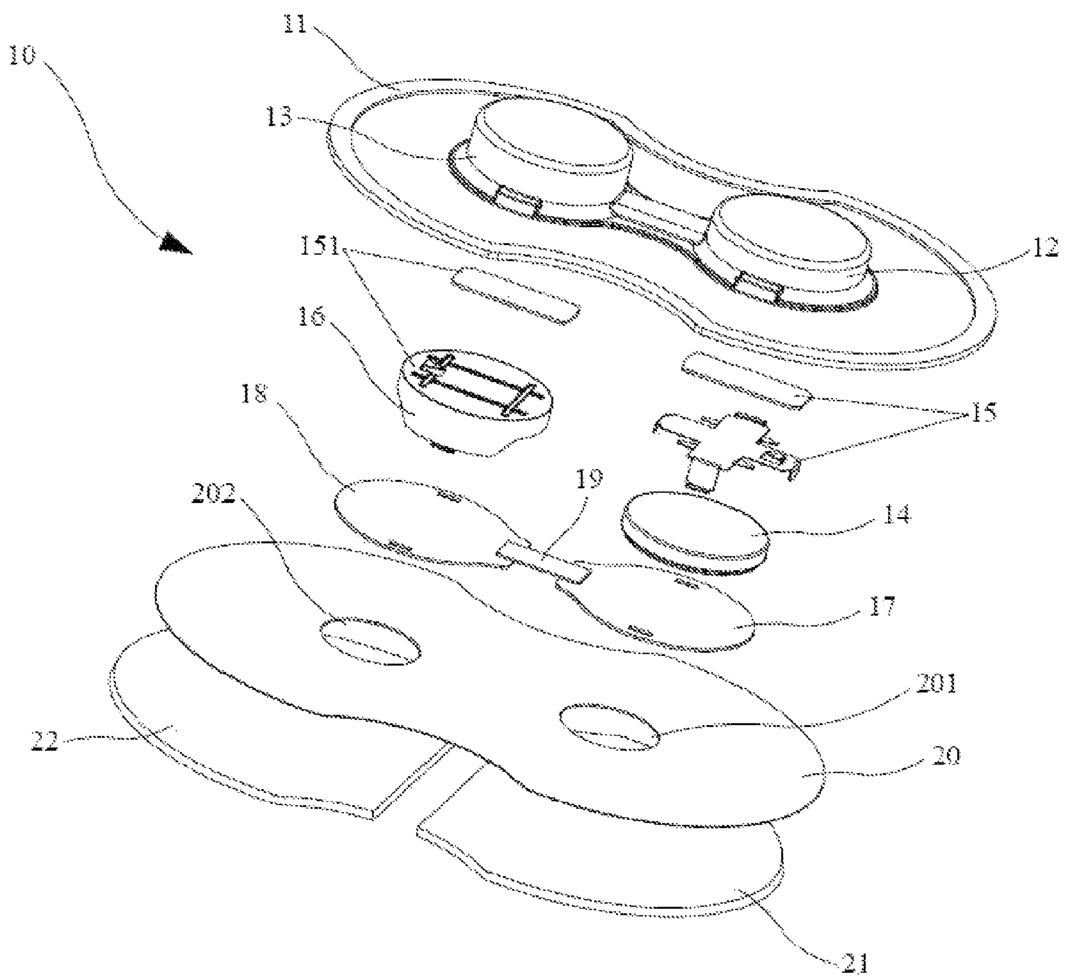
FIG. 1 is an exploded structural view of a conventional electronic low-frequency pulse patch of a one-piece structure.
Figure 2:
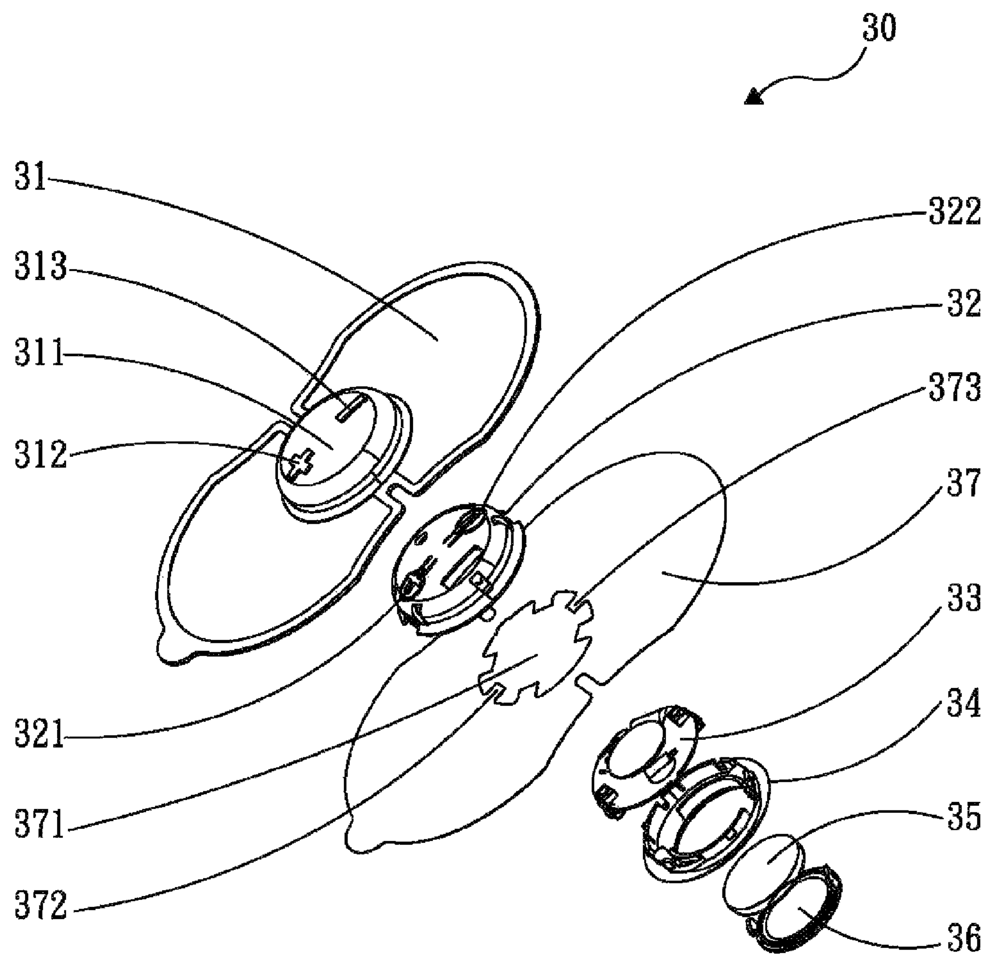
FIG. 2 is an exploded structural view of an electronic low-frequency pulse patch of a one-piece structure of the present invention.

FIG. 2 illustrates an exploded structural view of an electronic low-frequency pulse patch of a one-piece structure of the present invention. As shown, the electronic low-frequency pulse patch of a one-piece structure 30 primarily consists of a flexible top cover body 31, a hollow supporting enclosure 32, a control circuit unit 33, a base 34, a power supply unit 35 and a coupling output conductive flexible film 37. The flexible top cover body 31, which functions as an enclosure, may be made of either of a flexible water-proof silicone material and a TPU material. On the flexible top cover body 31 are formed a first symbol 312, which is a "+" sign, and a second symbol 313, which is a "–" sign, although they may also be replaced with any symbols. The flexible top cover body 31 has a receiving space 311 formed therein. Additionally, the first symbol 312 and the second symbol 313 may both be a relief symbol to make it easier for those visually impaired to know meanings represented by the first symbol 312 and the second symbol 313 by touching them.

Figure 3:
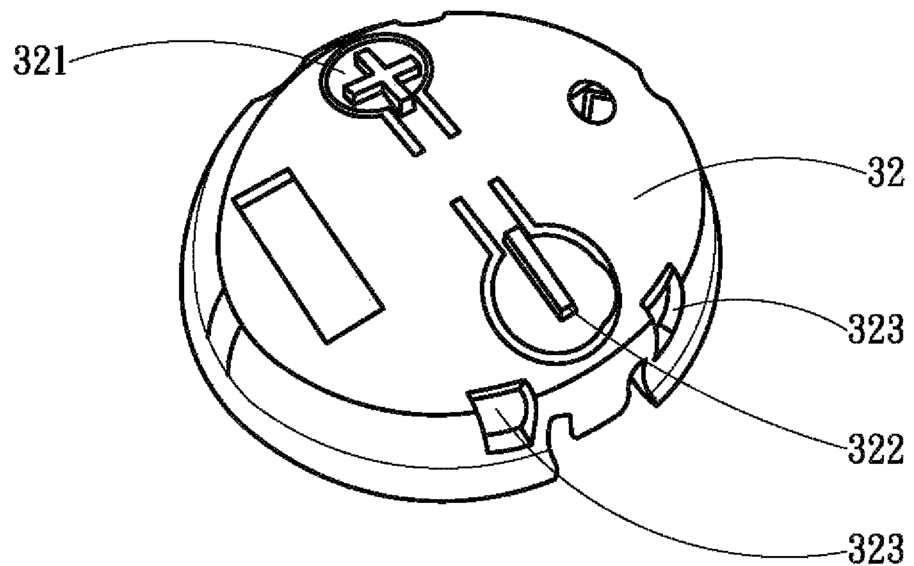
FIG. 3 is a schematic outline view of a hollow supporting enclosure of the present invention.

The hollow supporting enclosure 32 is disposed within the receiving space 311. A first cantilever elastic pushing end 321 and a second cantilever elastic pushing end 322 are disposed on the hollow supporting enclosure 32 in such a way that both the first cantilever elastic pushing end 321 and the second cantilever elastic pushing end 322 are coupled to an inner surface of the flexible top cover body 31, with positions of the first cantilever elastic pushing end 321 and the second cantilever elastic pushing end 322 corresponding to those of the first symbol 312 and the second symbol 313 respectively. Both the first cantilever elastic pushing end 321 and the second cantilever elastic pushing end 322 are of an elastic cantilever design, so when being pushed, they will elastically return back to the original positions to allow for another pushing operation for triggering. Also, to avoid confusion during assembly, the first cantilever elastic pushing end 321 and the second cantilever elastic pushing end 322 may be provided with the first symbol 312 and the second symbol 313 respectively on a respective surface thereof. In this way, reversed assembled positions of the first cantilever elastic pushing end 321 and the second cantilever elastic pushing end 322 can be avoided. Referring to FIG. 3 together, a plurality of through-slots 323 is disposed at a periphery of the hollow supporting enclosure 32 to facilitate integral joining of the hollow supporting enclosure 32 and the base 34.

Figure 4A:
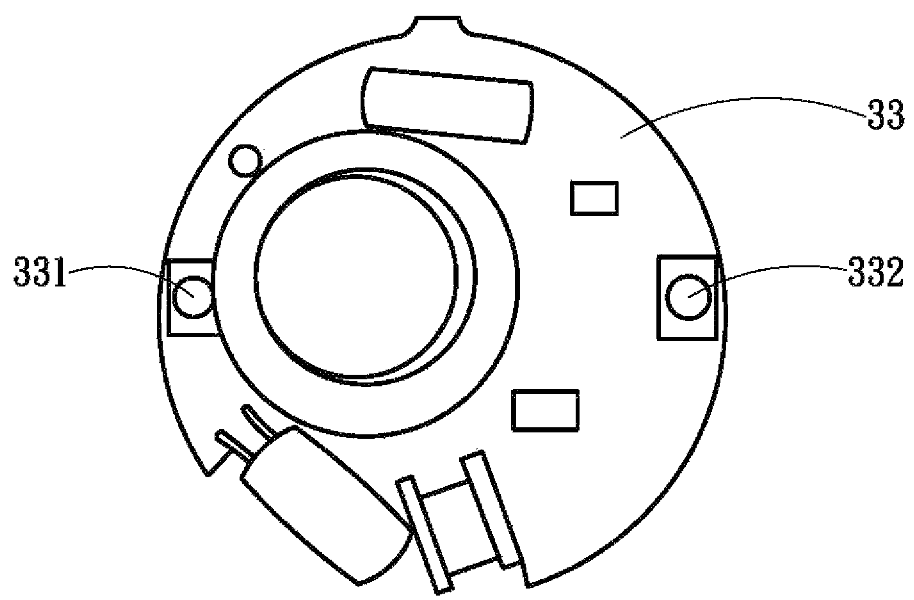
FIG. 4(*a*) is a schematic front outline view of a control circuit unit of the present invention.
Figure 4B:
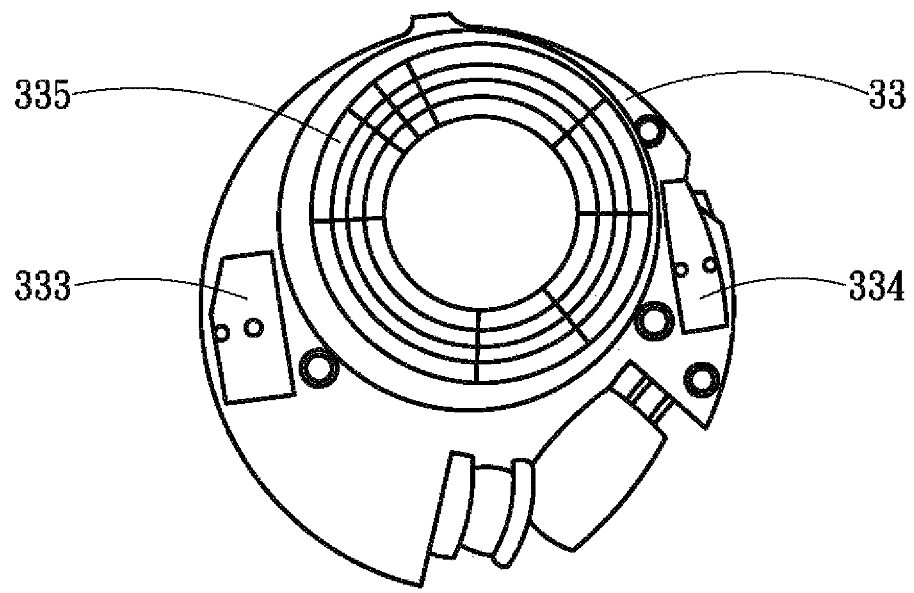

Referring to FIG. 4(*a*) and FIG. 4(*b*) together, the control circuit unit 33 is disposed within the hollow supporting enclosure 32, and is provided with at least one first low-frequency pulse output end 333, at least one second low-frequency pulse output end 334 as well as a first control end 331 and a second control end 332. The first control end 331 and the second control end 332 are coupled to the first elastic cantilever pushing end 321 and the second elastic cantilever pushing end 322 of the hollow support enclosure 32 respectively so that pulses outputted from the at least one first low-frequency pulse output end 333 and the at least one second low-frequency pulse output end 334 can be adjusted according to the number of times that the first elastic cantilever pushing end 321 and the second elastic cantilever pushing end 322 are triggered. The control circuit unit 33 is electrically coupled to the power supply unit 35 to supply power necessary for operation of the control circuit unit 33. Additionally, the control circuit unit 33 may further be provided with a power contact end 335 so as to be electrically connected to the power supply unit 35 directly.

Figure 5:
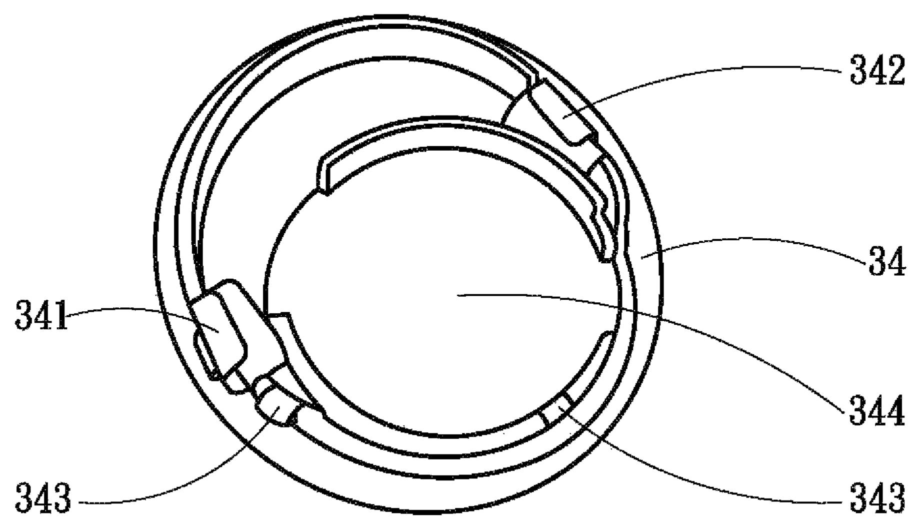
FIG. 5 is a schematic outline view of a base of the present invention.

The base 34 is joined to the bottom of the hollow supporting enclosure 32 to fix the control circuit unit 33 and the power supply unit 35 into the hollow supporting enclosure 32. Referring to FIG. 5 together, on the base 34 are disposed at least one first conductive end 341 electrically coupled to the at least one first low-frequency pulse output end 333 of the control circuit unit 33 and at least one second conductive end 342 electrically connected to the at least one second low-frequency pulse output end 334. This represents that the electronic low-frequency pulse patch of a one-piece structure 30 of the present invention has one or more sets of positive & negative outputs (i.e., the first low-frequency pulse output end 333 is considered as a positive output, and the second low-frequency pulse output end 334 is considered as a negative output). Additionally, at a periphery of the base 34 is disposed a plurality of elastic snap-fitting pieces 343 adapted to be elastically snap-fitted into the through-slots 323 of the hollow supporting enclosure 32 so that the base 34 and the hollow supporting enclosure 32 can be joined into one piece firmly. Furthermore, the base 34 may be formed with a through-hole 344, which can be closed by a bottom cover body 36, at a center thereof to facilitate replacement of the power supply unit 35 when the power level becomes insufficient. The power supply unit 14 may be any of a button cell, a lithium cell and a mercury cell.

Figure 6:
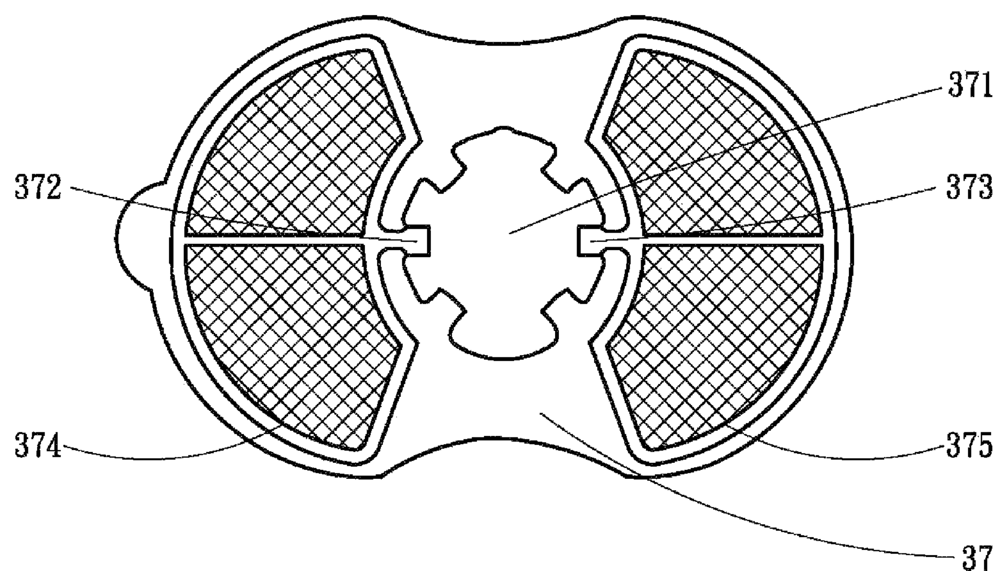
FIG. 6 is a schematic outline view of a coupling output conductive flexible film of the present invention.
Figure 7:
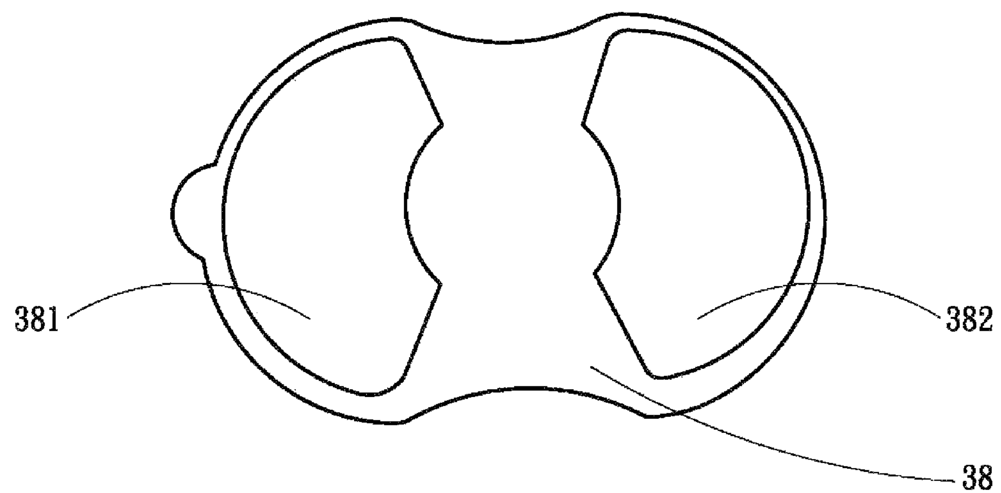
FIG. 7 is a schematic outline view of a protective layer of the present invention.

The coupling output conductive flexible film 37 is joined integrally to the bottom of the flexible top cover body 31 and is formed with an opening 371 at a center thereof. At a periphery of the opening 371 are disposed at least one first conductive contact lug 372 electrically connected to the at least one first conductive end 341 of the base 34 and at least one second conductive contact lug 373 electrically connected to the at least one second conductive end 342 of the base 34. Referring to FIG. 6 together, on a bottom surface of the coupling output conductive flexible film 37 are further disposed a first low-frequency pulse output region 374 electrically connected to the at least one first conductive contact lug 372 and a second low-frequency pulse output region 375 electrically connected to the at least one second conductive contact lug 373. Additionally, the coupling output conductive flexible film 37 is made of PET, and the first low-frequency pulse output region 374 and the second low-frequency pulse output region 375 disposed on the bottom surface thereof are made of a printed conductive material. Further, the coupling output conductive flexible film 37 may be formed by a first conductive flexible film and a second conductive flexible film that are bilaterally symmetric with each other in combination, with the opening 371 being disposed therebetween. The at least one first conductive contact lug 372 is disposed at a periphery of the opening 371 in the first conductive flexible film, and at least one second conductive contact lug 373 is disposed at a periphery of the opening 371 in the first conductive flexible film. The first low-frequency pulse output region 374 and the second low-frequency pulse output region 375 are disposed on respective bottom surfaces of the first conductive flexible film and the second conductive flexible film respectively.

In the electronic low-frequency pulse patch of a one-piece structure 30 of the present invention, the flexible top cover body 31 is used as an enclosure, the coupling output conductive flexible film 37 is attached, by virtue of the self-adhesion property thereof, onto the bottom of the flexible top cover body 31, and the first low-frequency pulse output region 374 and the first low-frequency pulse output region 375 are disposed at both sides of the coupling output conductive flexible film 37, so the electronic low-frequency pulse patch of a one-piece structure 30 is bendable and can be bent to conform to different curvature of different sites of the human body without use of any screw or other means for fixing.

Additionally, because the electronic low-frequency pulse patch of a one-piece structure 30 of the present invention has the power supply unit 35 and the hollow supporting enclosure 32 integrated into the flexible top cover body 31, the volume thereof is remarkably decreased as compared to common low-frequency massage pads. This makes the patch cheaper to manufacture and more convenient to be carried about, and the one-piece design in which the coupling output conductive flexible film 37 is attached to the flexible top cover body 31 provides a better water-proof effect, all of which make the patch very convenient to use.

Furthermore, in the electronic low-frequency pulse patch of a one-piece structure 30 of the present invention, electrical conduction is accomplished by electrically connecting the at least one first conductive end 341 and the at least one second conductive end 342 of the base 34 to the at least one first conductive contact lug 372 and the at least one second conductive contact lug 373 of the coupling output conductive flexible film 37 respectively, so when electrically connected, the at least one first conductive contact lug 372 and the at least one second conductive contact lug 373 will be pushed upwards by and attached integrally to the at least one first conductive end 341 and the at least one second conductive end 342 of the base 34 to form a conductive bridge structure. On the other hand, the at least one first conductive contact lug 372 and the at least one second conductive contact lug 373 are warped to contact the at least one first conductive end 341 and the at least one second conductive end 342 respectively when the coupling output conductive flexible film 37 being joined integrally to the bottom of the flexible top cover body 31. Therefore, by joining the hollow supporting enclosure 32 to the base 34, the structure can be fixed to make the bridge structure less likely to get loose due to the warping recovering force of the at least one first conductive contact lug 372 and the at least one second conductive contact lug 373. Thus, use of the conventional flexible ribbon cable is eliminated, and when the electronic low-frequency pulse patch of a one-piece structure 30 is bent, the junction will not be bent accordingly. This can avoid occurrences of damage and open-circuit faults, thereby prolonging the service life of the patch.

When the electronic low-frequency pulse patch of a one-piece structure 30 of the present invention is to be used, after the patch 30 is attached to a specific site of a human body, the user may press the first symbol 312 to trigger the first cantilever elastic pushing end 321 and the first control end 331. As a result, power necessary for outputting low-frequency pulses from the first low-frequency pulse output region 374 is supplied by the power supply unit 35 through the first low-frequency pulse output end 333, the first conductive end 341 and the first conductive contact lug 372 and, further through the second low-frequency pulse output region 375, the second conductive contact lug 373, the second conductive end 342 and the second low-frequency pulse output end 334, an electrical circuit is completed with the first low-frequency pulse output region 374 and the second low-frequency pulse output region 375 in contact with the human body serving as a negative electrode and a positive electrode respectively of the electrical circuit. Thus, electronic pulses (low-frequency) generated by the circuit control unit 33 are transferred to the human body for purpose of pain relieving and rehabilitation treatment.

Additionally, below the coupling output conductive flexible film 37 may be disposed a coupling conductive patch assembly 38, which includes a first coupling conductive patch 381 that can be adhered correspondingly to the first low-frequency pulse output region 374 and a second coupling conductive patch 382 that can be adhered correspondingly to the second low-frequency pulse output region 375. This can prevent electronic pulses (low-frequency) generated by the circuit control unit 33 from being applied directly onto the human body so as to cushion the impact strength of the electronic pulses (low-frequency) or mitigate the burning sensation.

Electronic pulse waveforms applicable to pain relieving treatment are categorized into: (1) dense wave, which is commonly used for pain relief, sedation, alleviation of spasm of muscles and blood vessels, and acupuncture anesthesia; (2) sparse wave, which is commonly used for treatment of atrophy and damage of various muscles, joints, ligaments or muscle tendons; (3) spare-dense wave, which is formed by sparse waves and dense waves appearing alternately and is commonly used for pain relief as well as treatment of sprains and strains, periarthritis, disorder of circulation of Qi and blood, ischialgia, facial paralysis, myasthenia and local frostbites; (4) sawtooth wave, which is a kind of fluctuating wave formed by modulating pulse amplitudes with a sawtooth form and may be used to stimulate phrenic nerves for purpose of artificial electro-respiration or for rescuing a patient suffering from respiratory failure, and also functions to enhance neuromuscular irritability, regulate functions of meridians and collaterals, and improve circulation of Qi and blood; (5) discontinuous wave, which is a kind of sparse wave that varies automatically in a rhythmic and intermittent manner and is commonly used for treatment of atrophy and paralysis and also for electro-muscle gymnastic exercises. Hence, the electronic low-frequency pulse patch of a one-piece structure 30 of the present invention may also provide various electronic pulse waves for pain relief and treatment by adjusting the number of times that the first control end 331 and the second control end 332 are triggered, and this setting process or approach may be built into the circuit control unit 33. Thus, the user may adjust the low-frequency wave into a necessary waveform depending on his or her own symptom, which represents a very humane design.

Figure 8:
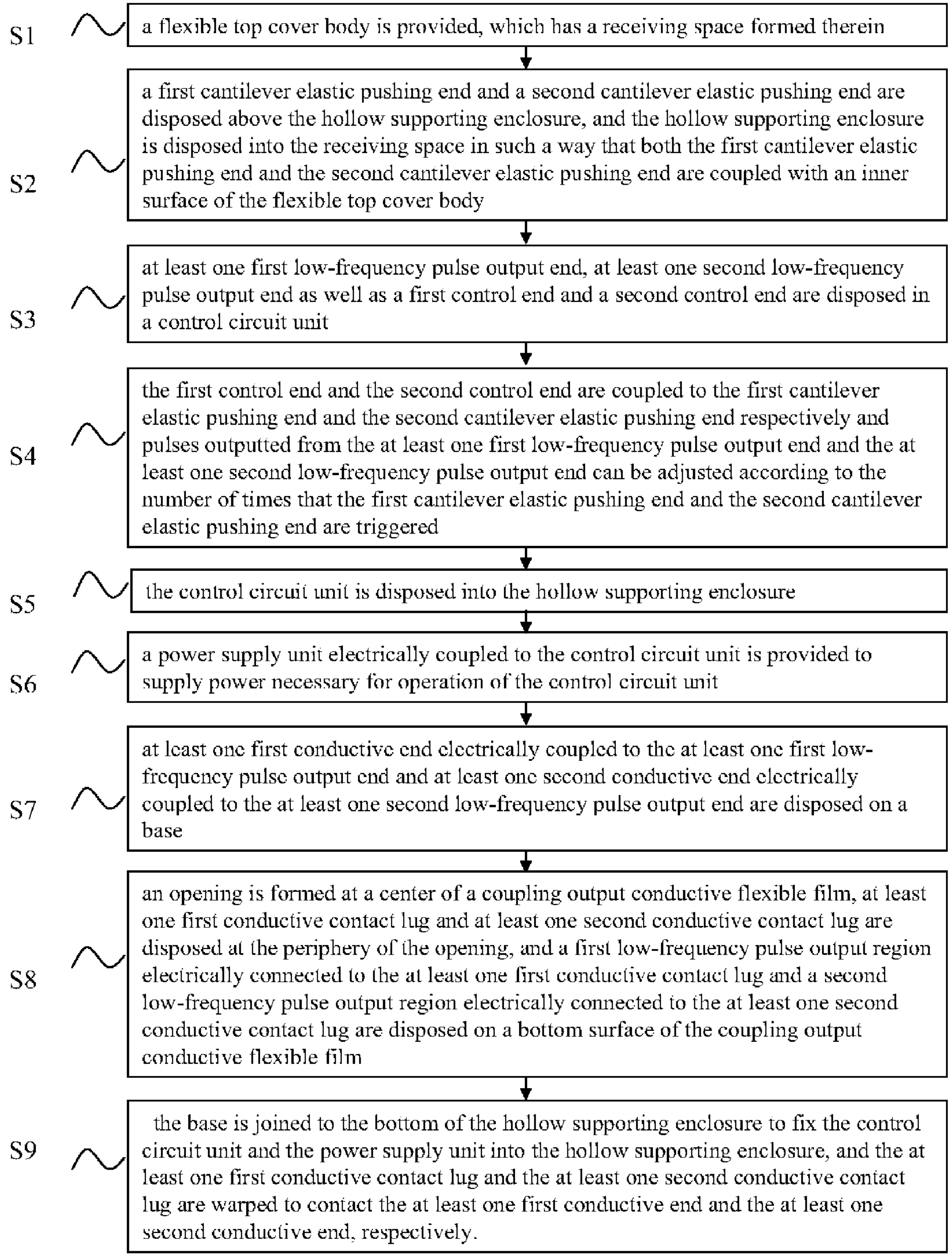
FIG. 8 is a flowchart of a method for manufacturing an electronic low-frequency pulse patch of a one-piece structure of the present invention.

Referring to FIG. 8, there is shown a flowchart of a method for manufacturing an electronic low-frequency pulse patch of a one-piece structure of the present invention. As shown, firstly, a flexible top cover body is provided, which has a receiving space formed therein (step S1). Then, a first cantilever elastic pushing end and a second cantilever elastic pushing end are disposed above the hollow supporting enclosure, and the hollow supporting enclosure is disposed into the receiving space in such a way that both the first cantilever elastic pushing end and the second cantilever elastic pushing end are coupled with an inner surface of the flexible top cover body (step S2). Next, at least one first low-frequency pulse output end, at least one second low-frequency pulse output end as well as a first control end and a second control end are disposed in a control circuit unit (step S3), and the first control end and the second control end are coupled to the first cantilever elastic pushing end and the second cantilever elastic pushing end respectively and pulses outputted from the at least one first low-frequency pulse output end and the at least one second low-frequency pulse output end can be adjusted according to the number of times that the first cantilever elastic pushing end and the second cantilever elastic pushing end are triggered (step S4). Subsequent to step S4, the control circuit unit is disposed into the hollow supporting enclosure (step S5), and a power supply unit electrically coupled to the control circuit unit is provided to supply power necessary for operation of the control circuit unit (step S6). Subsequent to step S6, at least one first conductive end electrically coupled to the at least one first low-frequency pulse output end and at least one second conductive end electrically coupled to the at least one second low-frequency pulse output end are disposed on a base (step S7). Thereafter, an opening is formed at a center of a coupling output conductive flexible film, at least one first conductive contact lug and at least one second conductive contact lug are disposed at the periphery of the opening, and a first low-frequency pulse output region electrically connected to the at least one first conductive contact lug and a second low-frequency pulse output region electrically connected to the at least one second conductive contact lug are disposed on a bottom surface of the coupling output conductive flexible film (step S8). Finally, the base is joined to the bottom of the hollow supporting enclosure to fix the control circuit unit and the power supply unit into the hollow supporting enclosure, and the at least one first conductive contact lug and the at least one second conductive contact lug are warped to contact the at least one first conductive end and the at least one second conductive end, respectively. (step S9).

The aforementioned flexible top cover body may be made of either of a flexible water-proof silicone material and a TPU material. On the flexible top cover body are formed a first symbol, which is a "+" sign, and a second symbol, which is a "−" sign. The first symbol and the second symbol may both be a relief symbol to make it easier for those visually impaired to identify them by touching. The hollow supporting enclosure is formed, at a periphery thereof, with a plurality of through-slots for a plurality of elastic snap-fitting pieces disposed at a periphery of the base to be integrally snap-fitted therein and to fix the bridge structure. The at least one first conductive contact lug is electrically connected to the at least one first conductive end, and the at least one second conductive contact lug is electrically connected to the at least one second conductive end. Additionally, the coupling output conductive flexible film is made of PET, and the first low-frequency pulse output region and the second low-frequency pulse output region disposed on the bottom surface thereof are made of a printed conductive material. Furthermore, a coupling conductive patch assembly may be disposed beneath the coupling output conductive flexible film, including a first coupling conductive patch that may be correspondingly adhered to the first low-frequency pulse output region and a second coupling conductive patch that may be correspondingly adhered to the second low-frequency pulse output region, which can prevent electronic pulses (low-frequency) generated by the circuit control unit from being applied directly onto the human body so as to cushion the impact strength of the electronic pulses (low-frequency) or mitigate the burning sensation.

I claim:

1. An electronic low-frequency pulse patch of a one-piece structure, comprising:

a flexible top cover body having a receiving space formed therein;

a hollow supporting enclosure being disposed in the receiving space, wherein above the hollow supporting enclosure are disposed a first cantilever elastic pushing end and a second cantilever elastic pushing end, both of which are coupled to an inner surface of the flexible top cover body;

a control circuit unit being disposed within the hollow supporting enclosure, wherein the control circuit unit is provided with at least one first low-frequency pulse output end, at least one second low-frequency pulse output end as well as a first control end and a second control end, and the first control end and the second control end are coupled to the first cantilever elastic pushing end and the second cantilever elastic pushing end respectively so that, according to the number of times that the first cantilever elastic pushing end and the second cantilever elastic pushing end are triggered, pulses outputted from the at least one first low-frequency pulse output end and the at least one second low-frequency pulse output end are adjusted;

a power supply unit being electrically coupled to the control circuit unit to supply power necessary for operation of the control circuit unit;

a base being joined to the bottom of the hollow supporting enclosure to fix the control circuit unit and the power supply unit into the hollow supporting enclosure, wherein the base is provided with at least one first conductive end electrically coupled to the at least one first low-frequency pulse output end and at least one second conductive end electrically coupled to the at least one second low-frequency pulse output end; and a coupling output conductive flexible film being joined integrally to the bottom of the flexible top cover body, wherein the coupling output conductive flexible film is formed with an opening at center and at a periphery of the opening are disposed at least one first conductive contact lug electrically connected to the at least one first conductive end and at least one second conductive contact lug electrically connected to the at least one second conductive end, and on a bottom surface of the coupling output conductive flexible film are disposed a first low-frequency pulse output region electrically connected to the at least one first conductive contact lug and a second low-frequency pulse output region electrically connected to the at least one second conductive contact lug; wherein the at least one first conductive contact lug and the at least one second conductive contact lug are warped to contact the at least one first conductive end and the at least one second conductive end respectively when the coupling output conductive flexible film being joined integrally to the bottom of the flexible top cover body.

2. The electronic low-frequency pulse patch of claim 1, wherein the flexible top cover body is made of a flexible water-proof silicone material or a TPU material.

3. The electronic low-frequency pulse patch of claim 1, wherein the coupling output conductive flexible film is made of polyester (PET), and the first low-frequency pulse output region and the second low-frequency pulse output region disposed on a bottom surface thereof are made of a printed conductive material.

4. The electronic low-frequency pulse patch of claim 1, wherein the power supply unit is a button cell or a lithium cell.

5. The electronic low-frequency pulse patch of claim 1, wherein a first symbol and a second symbol are formed on the flexible top cover body.

6. The electronic low-frequency pulse patch of claim 5, wherein the first symbol is a "+" sign and the second symbol is a "−" sign, and both the first symbol and the second symbol are a relief symbol.

7. The electronic low-frequency pulse patch of claim 1, wherein the hollow supporting enclosure is formed at a periphery thereof with a plurality of through-slots to be integrally joined with a plurality of elastic snap-fitting pieces disposed at a periphery of the base, and to fix a bridge structure of the at least one first conductive contact lug electrically connected to the at least one first conductive end and the at least one second conductive contact lug electrically connected to the at least one second conductive end.

8. The electronic low-frequency pulse patch of claim 1, wherein beneath the coupling output conductive flexible film is disposed a coupling conductive patch set, which includes a first coupling conductive patch that is correspondingly adhered to the first low-frequency pulse output region and a second coupling conductive patch that is correspondingly adhered to the second low-frequency pulse output region.

9. The electronic low-frequency pulse patch of claim 1, wherein the base is further formed with a through-hole at a center thereof, and the through-hole is closed by a bottom cover body.

10. A method for manufacturing an electronic low-frequency pulse patch of a one-piece structure, comprising the following steps:

providing a flexible top cover body, which has a receiving space formed therein;

disposing above a hollow supporting enclosure a first cantilever elastic pushing end and a second cantilever elastic pushing end, and disposing the hollow supporting enclosure into the receiving space in such a way that both the first cantilever elastic pushing end and the second cantilever elastic pushing end are coupled to an inner surface of the flexible top cover body;

disposing in a control circuit unit a first low-frequency pulse output end, a second low-frequency pulse output end as well as a first control end and a second control end in such a way that the first control end and the second control end are coupled to the first cantilever elastic pushing end and the second cantilever elastic pushing end respectively and pulses outputted from the first low-frequency pulse output end and the second low-frequency pulse output end are adjusted according to the number of times that the first cantilever elastic pushing end and the second cantilever elastic pushing end are triggered;

disposing the control circuit unit into the hollow supporting enclosure;

providing a power supply unit, which is electrically coupled to the control circuit unit to supply power necessary for operation of the control circuit unit;

disposing on a base a first conductive end electrically coupled to the first low-frequency pulse output end and a second conductive end electrically coupled to the second low-frequency pulse output end;

forming an opening at a center of a coupling output conductive flexible film, disposing at a periphery of the opening a first conductive contact lug and a second conductive contact lug, and disposing on a bottom surface of the coupling output conductive flexible film a first low-frequency pulse output region electrically connected to the first conductive contact lug and a second low-frequency pulse output region electrically connected to the second conductive contact lug; and joining the base to the bottom of the hollow supporting enclosure to fix the control circuit unit and the power supply unit into the hollow supporting enclosure, and warping the at least one first conductive contact lug and the at least one second conductive contact lug to contact the at least one first conductive end and the at least one second conductive end, respectively.

11. The method for of claim 10, wherein the flexible top cover body is made of a flexible water-proof silicone material or a TPU material.

12. The method of claim 10, wherein the coupling output conductive flexible film is made of PET, and the first low-frequency pulse output region and the second low-frequency pulse output region disposed on a bottom surface thereof are made of a printed conductive material.

13. The method of claim 10, wherein the power supply unit is a button cell or a lithium cell.

14. The method of claim 10, further comprising the step of forming a first symbol and a second symbol on the flexible top cover body.

15. The method of claim 14, wherein the first symbol is a "+" sign and the second symbol is a "−" sign, and both the first symbol and the second symbol are a relief symbol.

16. The method of claim 10, further comprising the step of forming a plurality of through-slots at a periphery of the hollow supporting enclosure and disposing a plurality of elastic snap-fitting pieces at a periphery of the base, so as to fix a bridge structure of the at least one first conductive contact lug electrically connected to the at least one first conductive end and the at least one second conductive contact lug electrically connected to the at least one second conductive end.

17. The method of claim 10, further comprising the step of disposing a coupling conductive patch assembly beneath the coupling output conductive flexible film.

18. The method of claim 17, wherein the coupling conductive patch assembly includes a first coupling conductive patch that is correspondingly adhered to the first low-frequency pulse output region and a second coupling conductive patch that is correspondingly adhered to the second low-frequency pulse output region.

19. The method of claim 10, further comprising the step of forming a through-hole at a center of the base and closing the through-hole by means of a bottom cover body.

* * * * *